US011911549B2

(12) United States Patent
Cotton et al.

(10) Patent No.: US 11,911,549 B2
(45) Date of Patent: Feb. 27, 2024

(54) PLASMAPHERESIS DEVICE

(71) Applicant: TSI TECHNOLOGY LIMITED, Loughborough (GB)

(72) Inventors: Stephen Cotton, Nottingham (GB); Terence Gourlay, Erskine (GB)

(73) Assignee: TSI TECHNOLOGY LIMITED, Loughborough (GB)

( * ) Notice: Subject to any disclaimer, the term of this patent is extended or adjusted under 35 U.S.C. 154(b) by 685 days.

(21) Appl. No.: 16/980,034

(22) PCT Filed: Mar. 12, 2019

(86) PCT No.: PCT/GB2019/050689
§ 371 (c)(1),
(2) Date: Sep. 11, 2020

(87) PCT Pub. No.: WO2019/175567
PCT Pub. Date: Sep. 19, 2019

(65) Prior Publication Data
US 2021/0015988 A1  Jan. 21, 2021

(30) Foreign Application Priority Data
Mar. 12, 2018 (GB) .................................. 1803914

(51) Int. Cl.
*A61M 1/34* (2006.01)
*A61M 1/36* (2006.01)
(52) U.S. Cl.
CPC ............ *A61M 1/3496* (2013.01); *A61M 1/34* (2013.01); *A61M 1/3601* (2014.02);
(Continued)

(58) Field of Classification Search
CPC ........ A61M 1/34; A61M 1/3496; A61M 1/36; A61M 1/3601; A61M 2202/0415;
(Continued)

(56) References Cited

U.S. PATENT DOCUMENTS 5,217,627 A * 6/1993 Pall ..................... A61M 1/0218
604/6.02
5,266,219 A * 11/1993 Pall ..................... B01D 39/163
210/488

(Continued)

FOREIGN PATENT DOCUMENTS

EP        0111620 A2    6/1984
EP        0139376 A1    5/1985
(Continued)

OTHER PUBLICATIONS

International Search Report and Written Opinion for corresponding Application No. PCT/GB2019/050689 (dated Jun. 17, 2019).
(Continued)

*Primary Examiner* — John Kim
(74) *Attorney, Agent, or Firm* — Troutman Pepper Hamilton Sanders LLP (Rochester)

(57) ABSTRACT

Apparatus for treating blood. A device (10) for separating plasma from blood comprises a blood flow path (20) including formations (24) for agitating blood flow along the blood flow path and a separation membrane (28) with a first surface in fluid communication with the blood flow path. The device may be comprised in an extracorporeal blood circuit and used in a method for separating plasma from blood.

26 Claims, 2 Drawing Sheets

(52) U.S. Cl.
CPC .............. *A61M 2202/0415* (2013.01); *A61M 2202/0427* (2013.01); *A61M 2202/0429* (2013.01); *A61M 2205/75* (2013.01)

(58) Field of Classification Search
CPC .. A61M 2202/0427; A61M 2202/0429; A61M 2205/75; A61M 2205/7518; A61M 2206/14
See application file for complete search history.

(56) References Cited

U.S. PATENT DOCUMENTS

| | | |
|---|---|---|
| 2004/0182783 A1 | 9/2004 | Walker et al. |
| 2008/0135502 A1 | 6/2008 | Pyo et al. |
| 2012/0175319 A1* | 7/2012 | Cotton ...................... A61J 1/10 210/806 |
| 2016/0007588 A1 | 1/2016 | Levesque et al. |

FOREIGN PATENT DOCUMENTS

| | | |
|---|---|---|
| EP | 0487576 A1 | 6/1992 |
| EP | 0487576 B1 | 2/1995 |
| WO | 89/06566 A1 | 7/1989 |

OTHER PUBLICATIONS

Search Report for corresponding Great Britain Application No. GB1803914.9 (dated Aug. 16, 2018).

* cited by examiner

PLASMAPHERESIS DEVICE

This application is a national stage application under 35 U.S.C. § 371 of PCT Application No. PCT/GB2019/050689, filed Mar. 12, 2019, which claims the priority benefit of Great Britain Patent Application No. 1803914.9, filed Mar. 12, 2018, which are hereby incorporated by reference in their entirety.

The present invention relates to devices and methods for separating plasma from blood, including for the treatment of sepsis.

Sepsis is a potentially life-threatening condition that occurs in response to an infection and which is characterised by systemic inflammation, multiple organ dysfunction and, in severe cases (ie septic shock), persistent low blood pressure, even following treatment with intravenous fluids. Sepsis is the most common cause of death in medical intensive care units and the tenth most common cause of death overall in the United States. The mortality rate from sepsis ranges from around 18% to over 50% depending on the stage at which treatment is initiated.

Sepsis treatment typically involves emergency hospitalisation and administration of antibiotics. The identification of the specific pathogen responsible for sepsis can take several days, and in many patients the causative agent is never identified. Accordingly, broad-spectrum antibiotics or a combination of narrow-spectrum antibiotics are used to treat sepsis, although these can have strong side-effects and are not always effective. In addition, this approach is becoming more problematic as antibiotic-resistant bacteria become more prevalent.

Apheresis is a new focus for the treatment of sepsis as a complement to standard treatment with antibiotics. These techniques aim to remove undesirable substances from the blood such as pro-inflammatory cytokines, microbial toxins and live or dead microbes. This may be achieved by techniques such as therapeutic plasmapheresis, which involves removing plasma from the blood and either treating the plasma to remove undesirable substances and then returning it to the blood, or replacing the plasma with donor plasma. Other techniques involve passing the blood through a cytokine or bacterial toxin adsorption filter in order to selectively remove undesirable substances directly from the blood. However, these techniques have so far proven to be of limited effectiveness in the treatment of sepsis.

There has now been devised a device for separating plasma from blood that overcomes or substantially mitigates the above mentioned and/or other problems associated with the prior art.

According to a first aspect of the invention, there is provided a device for separating plasma from blood, the device comprising:
 a blood flow path;
 a separation membrane having a first surface in fluid communication with the blood flow path; and
 formations located in the blood flow path for agitating blood flow along the blood flow path.

The device of this invention provides an efficient means of separating plasma from blood. In particular, the formations located in the blood flow path agitate, and in particular may create eddies and secondary flows, in the blood flow, which increases the rate at which plasma is separated from the blood by passing through the separation membrane.

The separation membrane may be substantially permeable to blood plasma but substantially impermeable to one or more other components of blood, such as red blood cells and platelets, in order to enable separation of blood plasma from the blood. In particular, the pores of the separation membrane may have an average pore size of at least 0.5 µm, 1 µm or 1.5 µm, no more than 5 µm, 4 µm or 3 µm, or around 2 µm. In particular, the average pore size may be between 0.5 µm and 5 µm, between 1 µm and 4 µm or between 1.5 µm and 3 µm.

The separation membrane preferably has a relatively high porosity in order to permit the efficient separation of plasma from blood without the need to subject blood cells to excessive stress in order to avoid causing red blood cell lysis and/or leukocyte activation. In particular, the separation membrane may have an air flow rate at 200 Pa of at least 10 $l/m^2$, at least 15 $l/m^2$ or at least 20 $l/m^2$.

The separation membrane may be a microporous membrane, a track-etched membrane or an ultrafiltration membrane. The separation membrane may be made of any suitable material, and may be polycarbonate, polyester, polyvinylidene fluoride, polyethersulfone, mixed cellulose esters, ultra-high molecular weight polyethylene, nylon polymer and/or PTFE. Suitable separation membranes include Polyethersulfone Membrane Filters supplied by Sartorius AG and Cyclopore® polycarbonate membrane supplied by GE Healthcare.

The blood flow path may be at least partially formed of a durable and rigid material and in particular may be formed of a plastics material. The blood flow path may be formed by any suitable technique such as injection moulding or 3D printing.

The blood flow path may be formed of a substantially transparent material or comprise a substantially transparent portion such that at least a portion of the blood flow path can be directly viewed by a user of the device, for example to ensure there is proper blood flow along the blood flow path.

A portion of the surface of the blood flow path may be formed of the first surface of the separation membrane. In particular, the separation membrane may form at least 20%, at least 30% or at least 40% of the surface area of the blood flow path.

The separation membrane may form, or at least partially form, a relatively lowest portion of the surface of the blood flow path when the device is in use such that separation of plasma from the blood may be aided by gravity.

The blood flow path may have a length that is significantly greater than its width and/or depth. This arrangement may increase the travel time of the blood along the blood flow path while in fluid communication with the separation membrane, and hence may improve the efficiency of plasma separation. In particular, the ratio between the length and the width and/or depth of the blood flow path may be at least 10:1, at least 50:1 or at least 100:1.

The blood flow path may have a generally rectangular, circular or elliptical transverse cross-section. The width of the blood flow path may be greater than its depth, such as in embodiments in which the blood flow path has a generally rectangular or elliptical transverse cross-section. In particular, the ratio between the width and the depth of the blood flow path may be at least 2:1, at least 5:1 or at least 10:1. In this arrangement, the separation membrane preferably at least partially forms one or both of the relatively larger upper and lower surfaces of the blood flow path.

The blood flow path may be convoluted and in particular may comprise one or more curved sections. The blood flow path may comprise a straight section located between each curved section, such that the blood flow path is made up of alternating straight and curved sections.

The curved sections of the blood flow path may produce a turn in the course of the blood flow path, and in particular may predominantly turn the course of the blood flow path by about 90 degrees, about 180 degrees, or between 90 and 180 degrees. The turns in the course of the blood flow path may predominantly alternate in direction such that at least a portion of the blood flow path follows a meandering course.

The straight sections of the blood flow path may have a length that is between half and double the width of the blood flow path, or that is approximately equal to the width of the blood flow path.

The formations located in the blood flow path may take any form that is suitable for creating agitation, such as eddies and secondary flows, in the blood flow along the blood flow path. The number and form of the formations located in the blood flow path may vary considerably, although the blood flow path preferably comprises multiple discreet formations that may be located at generally regular intervals along the length of the blood flow path.

The formations may constrict the transverse cross-section of the blood flow path, and in particular may constrict the transverse cross-section of the blood flow path by between around 10% and 90%, more preferably between around 20% and 80%, more preferably between around 30% and 70%, more preferably between around 40% and 60%, and more preferably around 50%.

The formations may be located in the blood flow path such that blood is able to pass on two opposing sides of each formation. In particular, the formations may extend from the relatively upper or relatively lower surface of the blood flow path and may extend through between around half the depth of the blood flow path and the full depth of the blood flow path.

The formations may comprise a substantially curved surface that faces upstream relative to the direction of blood flow through the blood flow path. The formations may also comprise a substantially flat surface that faces downstream relative to the direction of blood flow. The applicant has found that formations comprising a substantially curved surface that faces upstream and a substantially flat surface that faces downstream relative to the direction of blood flow to agitate blood flow in a way that provides particularly effective plasma separation. In particular, the formations preferably take the form of a prism of substantially semicircular cross section located in the blood flow path with the curved surface facing upstream relative to the direction of blood flow and the flat surface facing downstream relative to the direction of blood flow.

The formations are preferably located in straight sections of the blood flow path and are preferably not located in curved sections of the blood flow path. Formations may be present in at least a majority of the straight sections of the blood flow path.

The formations may be located approximately at the midpoint of the length of the straight sections of the blood flow path. In addition, the formations may be located in straight sections of the blood flow path upstream of a curved section of the blood flow path by a distance that is equal to no more than the width of the blood flow path and in particular that it equal to about half the width of the blood flow path. This positioning of the formations has been found to agitate blood flow in a way that provides particularly effective plasma separation.

The second surface of the separation membrane may be provided with a permeate carrier. The permeate carrier may be a porous hydrophilic material and in particular may be a fibrous material such as woven or nonwoven fabric formed of fibres of a hydrophilic material such as nylon.

The permeate carrier is preferably in contact with the second surface of the separation membrane such that the second surface of the separation membrane remains moist during the operation of the device, which facilitates the passage of the plasma that has been separated from the blood out of the pores on the second surface of the separation membrane and thus improves the efficiency of plasma separation.

The device may comprise an inlet, through which blood may enter the blood flow path, and an outlet, through which blood may exit the blood flow path. The inlet and outlet may permit a sealed connection between the blood flow path and medical tubing or an extracorporeal blood circuit, and in particular may comprise standard means for connection to medical tubing or an extracorporeal blood circuit, such as a Luer lock.

The device may comprise a means for generating a pressure differential across the separation membrane to facilitate the separation of plasma from the blood. The means may be capable of producing a transmembrane pressure of up to 20 mmHg, up to 30 mmHg or up to 40 mmHg. A transmembrane pressure of greater than 40 mmHg is preferably avoided in order to reduce the risk of causing red blood cell lysis and/or leukocyte activation.

In particular, the inlet may have a greater cross-sectional area than the outlet such that a back pressure is created in the blood flow path by the flow of blood from the inlet to the outlet.

The device is preferably capable of separating plasma from blood at a rate of at least 200 ml/hour, more preferably at least 400 ml/hour and more preferably at least 600 ml/hour.

Other than the inlet and outlet, the blood flow path may be sealed from the exterior of the device, in order to reduce the risk of contaminants from the external environment entering the blood as it passes through the blood flow path.

The device may further comprise a collector in fluid communication with the second surface of the separation membrane for collecting plasma separated from blood in the blood flow path. The collector preferably comprises a sealable container in order to prevent spillage of the plasma that has been separated from the blood.

The collector may be formed of a substantially transparent material or comprise a substantially transparent portion such that the interior of the collector can be directly viewed by a user of the device, for example to determine the quantity of plasma that has been separated from the blood.

The collector may contain an absorbent material for absorbing the plasma that has been separated from the blood. The absorbent material may be a superabsorbent material such as a polyacrylate and especially solid crystalline sodium polyacrylate. The sodium polyacrylate is preferably in the form of a sheet comprising sodium polyacrylate crystals encapsulated between two layers of carrier material, such as tissue paper. A specific example of a suitable material is Gelok® 14040S/S manufactured by Gelok International Corporation.

The superabsorbent material may convert the plasma that has been separated from the blood into a solid or semi-solid material that can be handled more easily than a liquid and disposed of by incineration, which is particularly advantageous with plasma that may be hazardous, such as plasma separated from the blood of a patient suffering from sepsis.

The collector may have a volume of between approximately 1 and 5 litres. The volume of the collector is preferably at least 50% greater than the volume of plasma that is expected to be collected in order to provide sufficient headspace to reduce the risk of spillage of plasma.

The collector may further comprise a vent that enables the passage of gas out of the collector in order to release any pressure that builds up in the collector as plasma passes through the separation membrane and takes up space in the container.

The device may be supplied in parts to be assembled prior to use, or in fully assembled configuration. The device may be reusable or a single-use disposable device. The device being single-use removes the need for sterilisation and ensures that no cross-contamination occurs between treatments.

The device may be used to separate plasma from a blood in order to produce a red blood cell concentrate, such as for transfusion, or in an extracorporeal blood circuit for the removal of plasma from the circulatory blood of a patient, for example for plasma donation or to remove undesirable substances contained in plasma from the blood, such as proinflammatory cytokines, microbial toxins and microbes in the treatment of sepsis.

According to a second aspect of this invention, there is provided an extracorporeal blood circuit comprising a device according to the first aspect of this invention.

The circuit according to this aspect of the invention may be for the extracorporeal separation of plasma from blood for example for the purposes of plasma donation or to remove undesirable substances contained in plasma from the blood. These undesirable substances may include proinflammatory cytokines, microbial toxins and live or dead microbes in the treatment of sepsis.

The extracorporeal blood circuit according to this aspect of the invention may be generally similar to a standard haemodialysis circuit. The circuit may comprise means for connecting the cardiovascular circulation of a patient to the device, for example through a vein or artery via either two needles or one double lumen needle. The circuit may further comprise a pump such as a peristaltic pump in order to facilitate blood flow through the circuit.

The extracorporeal blood circuit may further comprise a means for selectively removing undesirable substances from the blood, such as proinflammatory cytokines, microbial toxins and live or dead microbes. This may be located at any point in the extracorporeal circuit, but is preferably located downstream of the device. This may include a cytokine filter of the type disclosed in International Patent Application No PCT/GB2010/050061. This may also be a cloth filter such as woven, non-woven or three-dimensional textile filters. The cloth may be formed of or coated with a microporous, mesoporous or adsorbent material that may be capable of removing undesirable substances from the blood. In particular, the cloth filter may be a ceramic cloth such as activated carbon cloth.

The extracorporeal blood circuit may also comprise a means for determining the quantity of plasma that the device has removed from the blood and means for supplying fluid to the blood before it is returned to the patient. The means for determining the quantity of plasma removed from the blood and means for supplying fluid to the blood preferably communication with each other in order to autonomously supply substantially the same quantity of fluid to the blood as has been removed from the blood. The fluid that is supplied to the blood may be donor plasma or a plasma substitute.

The means for determining the quantity of plasma that the device has removed from the blood may be a means for determining the volume or mass of the plasma that the device has removed from the blood. In particular, as the device may increase in mass as plasma is separated from the blood and accumulates in the collector, the means may comprise a means for measuring the mass of the device.

The extracorporeal blood circuit preferably comprises a feedback loop with which the means for determining the quantity of plasma that the device has removed from the blood communicates. The feedback loop may comprise means, such as an electronic means, for calculating the quantity of fluid that is to be supplied to the blood. The feedback loop may then communicate with the means for supplying fluid to the blood, which may then supply the correct quantity of fluid to the blood. This system preferably operates continuously during the operation of the device.

According to a third aspect of this invention, there is provided a method of separating plasma from blood comprising the steps of:
  providing a device according to the first aspect of this invention;
  introducing blood into the blood flow path; and,
  removing the blood from the blood flow path.

The method according to this aspect of the invention may be an in vitro method, such as a method of separating plasma from a blood sample, for example in order to produce a blood cell concentrate.

The method according to this aspect of the invention may also be an extracorporeal method of separating plasma from blood. This may involve providing an extracorporeal blood circuit according to the second aspect of this invention.

The extracorporeal method of separating plasma from blood may be a method of treating a condition characterised by the presence of undesirable substances in the circulation. In particular, the extracorporeal method of separating plasma from blood may be a method of treating sepsis, in which case the undesirable substances removed from the blood may include proinflammatory cytokines, microbial toxins and live or dead microbes.

The extracorporeal method may be performed continuously for extended periods, and in particular may be performed for at least 2 hours, at least 4 hours, 8 hours or at least 16 hours.

The invention is now described in greater detail, by way of example only, with reference to the accompanying drawings, in which

Figure 1:
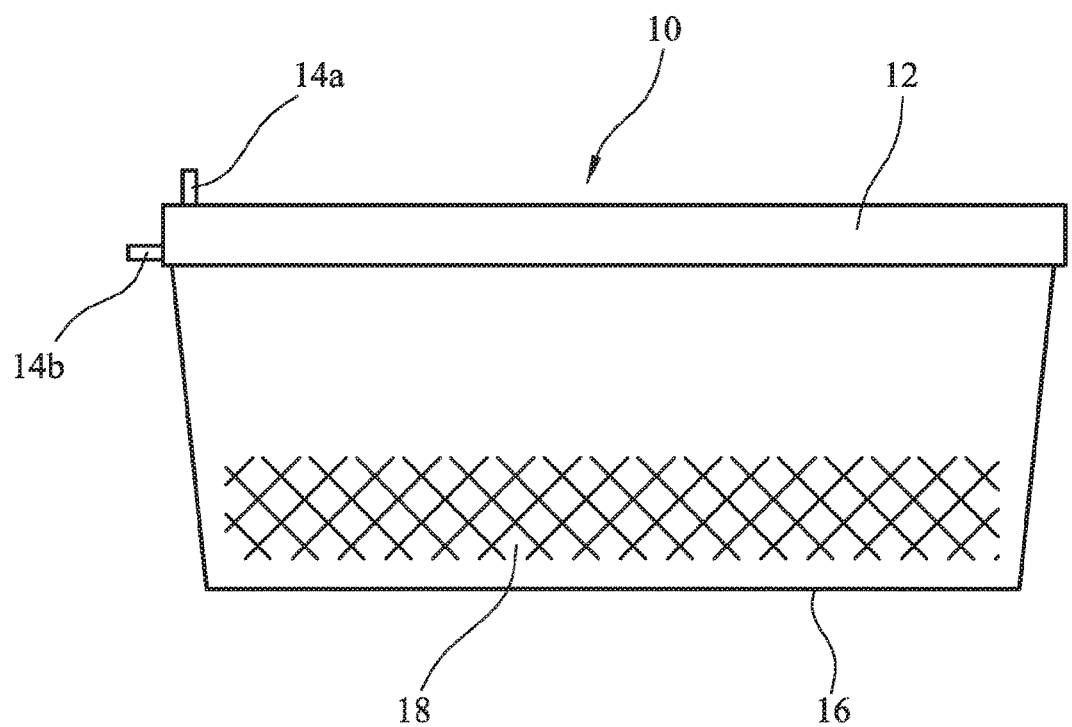
FIG. 1 is a side view, schematic and not to scale, of a device according to the first aspect of this invention.

Referring first to FIG. 1, a device 10 according to this invention comprises a separator 12 having an inlet port 14*a* and an outlet port 14*b*, and a collector 16 containing a superabsorbent material 18. The collector 16 is formed of transparent polycarbonate and is generally rectangular with an open top. The separator 12 fits over and engages with the rim of the open top of the collector 16 such that the open top of the collector 16 is closed by the separator 12 and the bottom surface of the separator 12 is exposed to the interior of the collector 16. The inlet port 14*a* extends upwardly from the upper surface of the separator 12 and the outlet port 14b extends outwardly from the lower part of the side surface of the separator 12.

Figure 2:
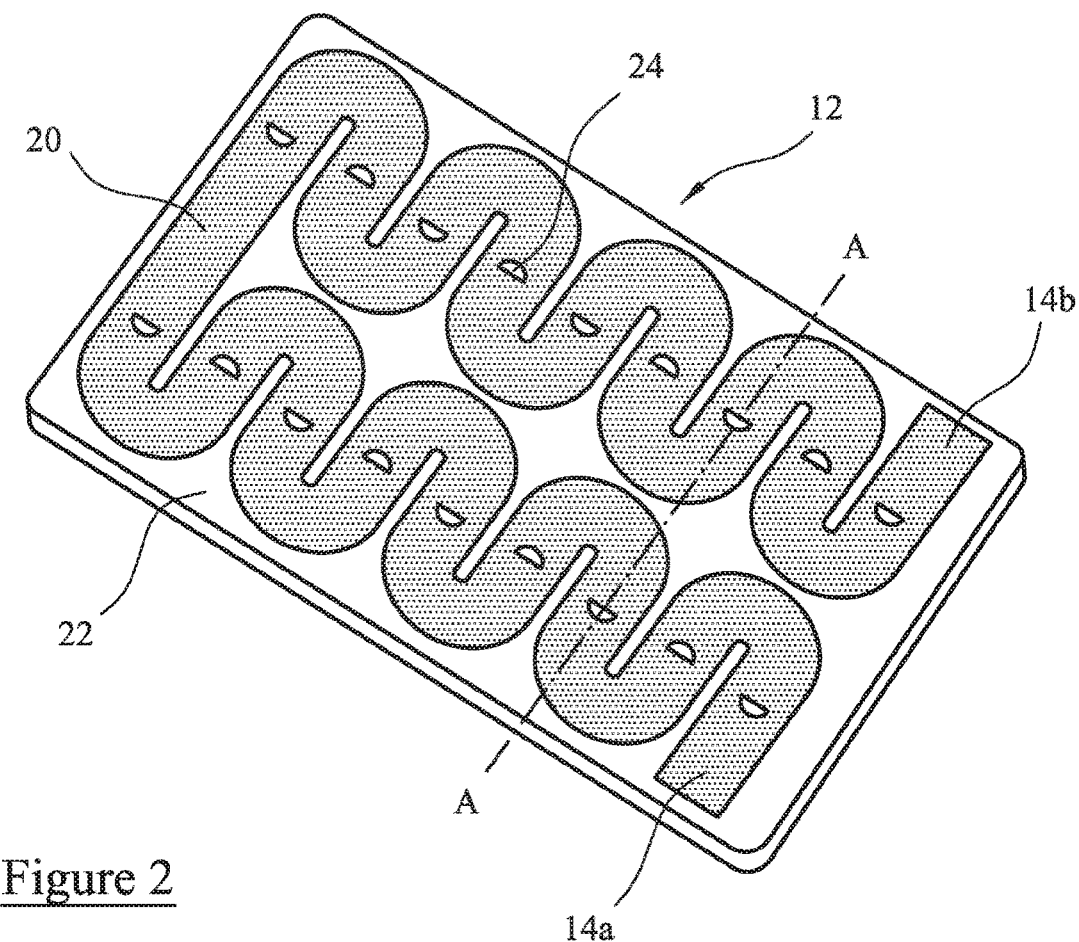
FIG. 2 is a perspective view, schematic and not to scale, of the separator of the device of FIG. 1.
Figure 3:
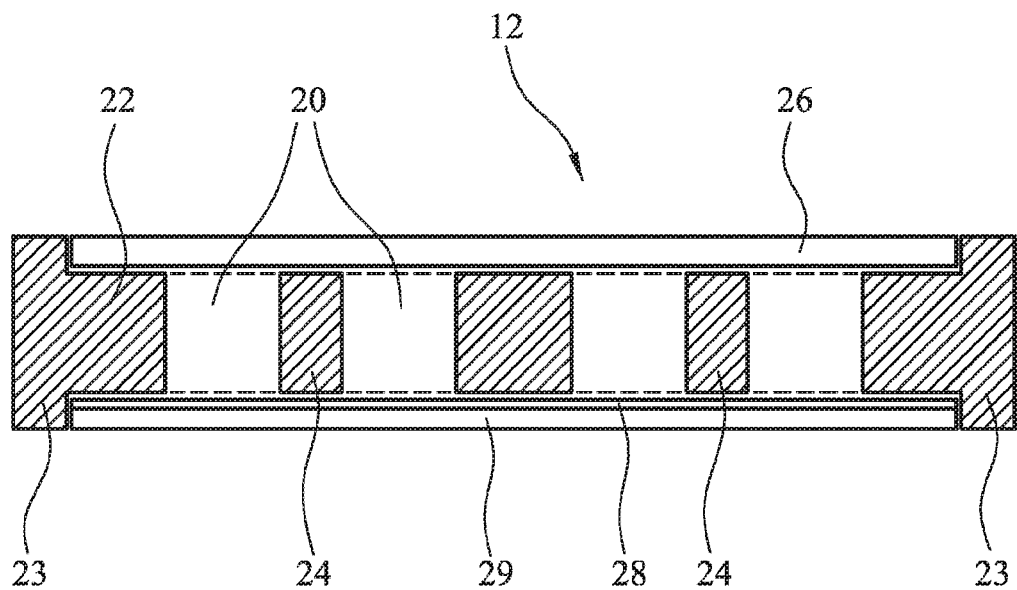
FIG. 3 is a cross-sectional view, schematic and not to scale, of the separator of FIG. 2 taken along line A-A; and, FIG. 4 is a flow chart depicting a method of treating blood according to this invention.

Referring now to FIGS. 2 and 3, the separator 12 comprises a frame 22, a lid 26 and a separation membrane 28. The frame 22 is formed of a moulded plastics material and has a generally rectangular outline that corresponds with the open top of the collector 16. The bottom surface of the frame 22 comprises a border 23 around its outer edge that engages with the rim of the collector 16. The border 23 and the rim of the collector 16 comprise cooperating formations (not shown) to aid the proper location of the separator 12 over the open top of the collector 16.

The frame 22 comprises a channel that is open on both the upper and lower surfaces of the frame 22 and follows a convoluted course made up of alternating straight sections and curved sections through the frame 22. The frame 22 further comprises formations 24 in the form of semi-circular prisms located in the channel with their curved surfaces facing the inlet port 14a and the flat surface facing the outlet port 14b. The formations 24 are located at the midpoint of each straight section of the channel. The frame 22 further comprises reinforcing ribs (not shown) that extend across the channel in order to connect the formations 24 to the remainder of the frame 22 and provide the frame 22 with a more rigid structure.

The lid 26 is securely attached to the upper surface of the frame 22 such that the lid 26 seals the open side of the channel on the upper surface of the frame 22. The lid 26 is formed of a transparent layer of polycarbonate and hence allows the interior of the channel to be viewed by a user of the device 10.

The separation membrane 28 is securely attached to the lower surface of the frame 22 such that the separation membrane 28 seals the open side of the channel on the lower surface of the frame 22. The separation membrane 28 is a polyethersulfone (PES) membrane filter with a high density of pores in the range of 2-3 microns in diameter. A permeate carrier 29 in the form of a thin sheet if nonwoven material formed of fine nylon fibres is attached to the lower surface of the separation membrane 28.

Accordingly, the blood flow path 20 is defined by the frame 22, which makes up the side surfaces of the blood flow path 20, the lid 26, which forms the upper surface of the blood flow path 20, and the separation membrane 28, which forms the lower surface of the blood flow path 20.

The device 10 may be used to treat blood by connecting the inlet port 14a to a source of the blood that is to be treated, and connecting the outlet port 14b to a blood collector for collecting the treated blood. The apparatus 10 may also be used to treat a patient by incorporating it into an extracorporeal blood treatment circuit. The inlet port 14a and outlet port 14b are suitable for engagement with standard connectors used in blood circuits.

Blood is introduced into the separator 12 via the inlet port 14a, passes along the blood flow path 20 in contact with the separation membrane 28 and is extracted from the separator 12 path via the outlet port 14b. As the blood passes along the blood flow path 20, a portion of the plasma passes through the separation membrane 28 and into the interior of the collector 16. The plasma that initially passes through the separation membrane 28 soaks into and saturates the permeate carrier 29 and then passes from the bottom surface of the permeate carrier 29 into the collector 16. Accordingly, the permeate carrier 29 keeps the bottom surface of the separation membrane 28 moist, which facilitates passage of plasma through the separation membrane 28 and hence improves the efficiency of plasma separation. The plasma that passes into the collector 16 is absorbed by the superabsorber 18 and can be disposed of by incineration after use of the device 10.

The outlet port 14b has a smaller bore than the inlet port 14a such that a pressure of around 40 mmHg is created across separation membrane 28 as blood passes along the blood-flow path. This transmembrane pressure further increases the efficiency of plasma transmission through the separation membrane 28 and into the container 16. The particularly high porosity of the separation membrane 28 improves the efficiency of plasma removal at these relatively low transmembrane pressures and hence eliminates the need to use higher transmembrane pressures that could risk causing red blood cell lysis or leukocyte activation.

The blood flow path 20 following a convoluted course maximises its length and hence the duration of exposure of the blood to the separation membrane 28, which increases the efficiency of plasma separation. In addition, the formations 24 create eddies and secondary flows in the blood flow as the blood passes along the blood flow path 20, which further increase the efficiency of plasma separation.

In particular, each of the features of the blood flow path comprising straight and curved sections, the formations being located at the midpoint of each straight section, and the formations in the form of semi-circular prisms with their curved surfaces facing upstream relative the direction of blood flow have been found provide particular improvements in plasma separation.

The apparatus is able to achieve a plasma removal rate in the range of 10 ml/min to 20 ml/min.

Figure 4:
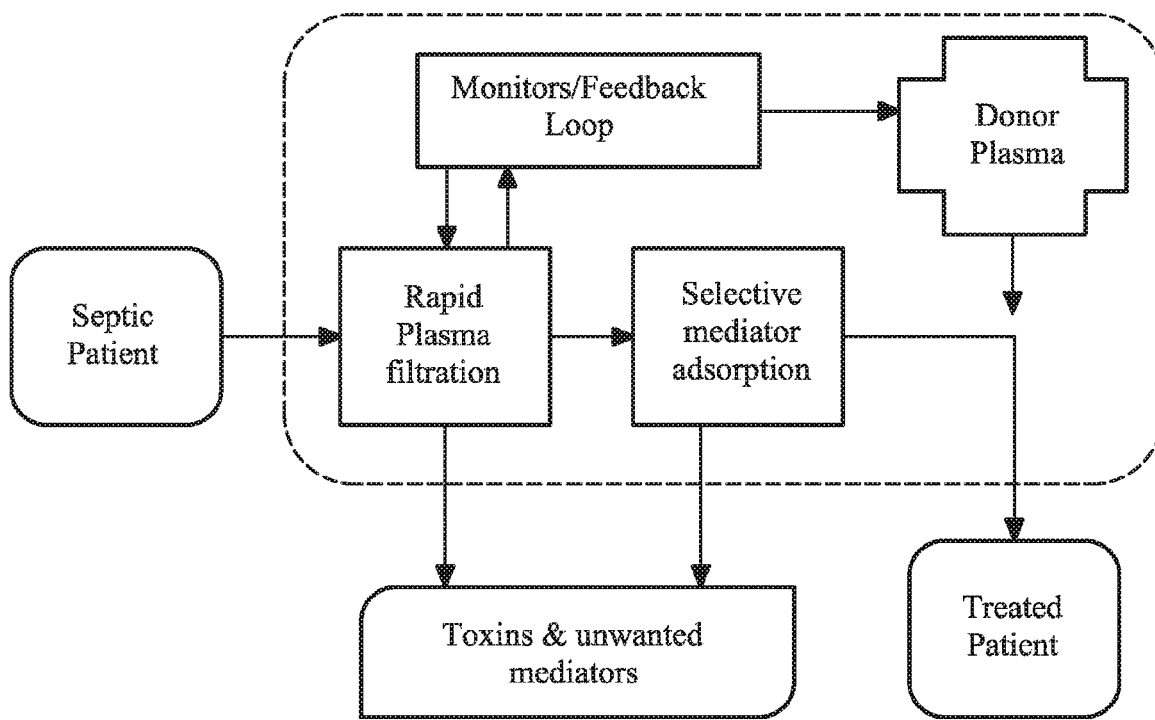

Referring now to FIG. 4, the apparatus is of particular utility in the treatment of a patient with sepsis by removing a portion of the plasma, which contains undesirable substances including proinflammatory cytokines, microbial toxins and live or dead microbes, from the circulation of the patient.

Blood from a patient having sepsis is supplied to the device 10, which separates a portion of the plasma, along with undesirable substances contained within the plasma, from the blood. The blood then passes to an additional filtration step that removes a portion of the proinflammatory cytokines, microbial toxins and microbes that remain in the blood. Suitable filtration devices include the filters disclosed in International Patent Application No PCT/GB2010/050061.

The device 10 is located on scales to enable its weight to be monitored in order to determine the quantity of plasma that has been separated from the blood. An automatic feedback loop then supplies the correct quantity of donor plasma to the blood to replace the septic plasma that has been removed. The treated blood is then returned to the patient's circulation. This patient may be treated in this way continuously for extended periods of time as a rescue treatment for sepsis.

Following treatment, the plasma that has been separated from the blood is in the form of solid waste following absorption by the superabsorbent material 18 and may thus be disposed of by incineration. This is particular advantageous as plasma that has been separated from the blood of a patient with sepsis is hazardous waste, which is generally problematic to dispose of in liquid form.

The invention claimed is:

1. A device for separating plasma from blood, the device comprising:
   a blood flow path having alternating straight and curved sections along a length thereof;

a separation membrane having a first surface in fluid communication with the blood flow path; and a plurality of discrete formations located in the straight sections of the blood flow path at generally regular intervals along the length of the blood flow path for agitating blood flow along the blood flow path.

2. The device of claim 1, wherein the separation membrane is substantially permeable to blood plasma but substantially impermeable to one or more other components of blood.

3. The device of claim 2, wherein the separation membrane has an average pore size of between 0.5 μm and 5 μm, between 1 μm and 4 μm, between 1.5 μm and 3 μm, or around 2 μm.

4. The device of claim 1 any preceding claim, wherein the separation membrane has an air flow rate at 200 Pa of at least 10 l/m², at least 15 l/m² or at least 20 l/m².

5. The device of claim 1, wherein blood flow path is formed of a substantially transparent material or comprises a substantially transparent portion.

6. The device of claim 1, wherein the separation membrane forms at least 20%, at least 30% or at least 40% of a surface area of the blood flow path.

7. The device of claim 1, wherein the separation membrane forms a relatively lowest portion of a surface of the blood flow path.

8. The device of claim 1, wherein a ratio between a length and a width of the blood flow path may be at least 10:1, at least 50:1 or at least 100:1.

9. The device of claim 1, wherein each curved section produces a turn in a course of the blood flow path of about 90 degrees, about 180 degrees, or between 90 and 180 degrees.

10. The device of claim 9, wherein the turns in the course of the blood flow path predominantly alternate in direction such that the blood flow path follows a meandering course.

11. The device of claim 1, wherein the straight sections of the blood flow path have a length that is between half and double a width of the blood flow path, or about equal to the width of the blood flow path.

12. The device of claim 1, wherein the formations constrict a transverse cross-section of the blood flow path by between around 10% and 90%, between around 20% and 80%, between around 30% and 70%, between around 40% and 60%, or around 50%.

13. The device of claim 1, wherein the formations comprise a substantially curved surface that faces upstream relative to a direction of blood flow through the blood flow path.

14. The device of claim 1, wherein the formations comprise a substantially flat surface that faces downstream relative to a direction of blood flow.

15. The device of claim 1, wherein the formations are not located in curved sections of the blood flow path.

16. The device of claim 1, wherein formations are located approximately at a midpoint of a length of the straight sections of the blood flow path.

17. The device of claim 1, wherein formations are located upstream of a curved section of the blood flow path by a distance that is equal to no more than a width of the blood flow path, or about equal to half the width of the blood flow path.

18. The device of claim 1, wherein the device further comprises a permeate carrier in contact with a second surface of the separation membrane.

19. The device of claim 18, wherein the permeate carrier is a layer of porous hydrophilic material.

20. The device of claim 1, wherein the device comprises an inlet, through which blood may enter the blood flow path, and an outlet, through which blood may exit the blood flow path.

21. The device of claim 20, wherein the inlet has a greater cross-sectional area than the outlet.

22. The device of claim 1, wherein the device comprises a collector in fluid communication with a second surface of the separation membrane for collecting plasma separated from blood in the blood flow path.

23. The device of claim 22, wherein the collector is formed of a substantially transparent material or comprise a substantially transparent portion.

24. The device of claim 22, wherein the collector contains a superabsorbent material.

25. The device of claim 24, where the superabsorbent material is a polyacrylate.

26. The device of any of claim 22, wherein the collector has a volume of between approximately 1 and 5 litres.

* * * * *